(12) United States Patent
James

(10) Patent No.: US 7,130,698 B2
(45) Date of Patent: Oct. 31, 2006

(54) APPARATUS FOR APPLYING PULSED VOLTAGE CHARGE TO LIVING MATTER

(76) Inventor: Robert G. James, P.O. Box 1531, Vieques, PR (US) 00765

( * ) Notice: Subject to any disclaimer, the term of this patent is extended or adjusted under 35 U.S.C. 154(b) by 314 days.

(21) Appl. No.: 10/798,036

(22) Filed: Mar. 11, 2004

(65) Prior Publication Data

US 2005/0203577 A1    Sep. 15, 2005

(51) Int. Cl.
*A61N 1/00*    (2006.01)
*A61N 5/00*    (2006.01)
(52) U.S. Cl. ............... 607/115; 607/96; 607/101; 606/32; 606/33
(58) Field of Classification Search ............ 607/88–91, 607/93, 96–101, 115; 606/8–12, 32–35, 606/41, 42; 315/111.21, 111.31, 111.81, 315/111.91; 313/231.31–231.61, 262.1
See application file for complete search history.

(56) References Cited

U.S. PATENT DOCUMENTS 5,184,046 A * 2/1993 Campbell ............... 315/111.21

| | | | |
|---|---|---|---|
| 5,300,097 A * | 4/1994 | Lerner et al. ............... | 607/93 |
| 5,616,140 A * | 4/1997 | Prescott ....................... | 606/10 |
| 6,328,760 B1 * | 12/2001 | James ........................ | 607/88 |
| 6,511,475 B1 * | 1/2003 | Altshuler et al. ............. | 606/9 |
| 6,669,627 B1 * | 12/2003 | Campbell et al. ............ | 600/27 |
| 6,958,063 B1 * | 10/2005 | Soll et al. .................... | 606/41 |

* cited by examiner

Primary Examiner—A. Farah
(74) Attorney, Agent, or Firm—Michael Bak-Boychuk

(57) ABSTRACT

Apparatus for inducing electrically charged alignment changes in biological tissue includes a generally flat translucent cavity containing a volume of gas that includes water vapor, carbon dioxide and other similarly common molecules that is charged along one surface by a sequence of pulses of electrical charge each of a potential sufficient to excite the common molecules to a higher state. The opposite side of the cavity is then conformed for intimate contact with the skin of a person, thus communicating the electromagnetic pulses associated with each excitation level change into the tissue.

1 Claim, 3 Drawing Sheets

APPARATUS FOR APPLYING PULSED VOLTAGE CHARGE TO LIVING MATTER

BACKGROUND OF THE INVENTION

1. Field of the Invention

The present invention relates to pulsed charge devices, and more particularly to pulse charged surfaces capacitively coupled to anatomical parts to induce electron state changes in the biological matter comprising same.

2. Description of the Prior Art

In my prior U.S. Pat. No. 6,328,760 issued on Dec. 11, 2001 I have described a plasma device conformed to ionize certain prevalent biological molecules and elements with the emission spectra of this ionization process then coupling efficiently with the dominant molecular structures in living matter. In consequence, repair and reconstruction of living cells is both accelerated and enhanced by the illumination with these selected spectra. Since that time I have discovered that a fully developed ionization process need not be utilized and an electrical potential between the living matter and the charge sufficient to change some of the electron states of the molecular combinations of living tissue may produce the necessary molecular lattice rearrangement to promote growth or healing.

Earlier I have observed that virtually all living functions entail electrical potential balances and the cell itself closely mimics a 'wet circuit'. Sporadic disruptions of these potential balances, either because of the introduction of some contaminant or as result of some unwanted change in the charge architecture, seem to be the causative events that lead to disease and it is the rearrangement of this charge architecture anomalies that appear to be at the heart of the process that I earlier described in the '760 us patent. Excepting, of course, those abnormalities that reach into the genome itself most of these electro-potential effects seem to be at the larger or macro level, such as those affecting the Na+/K+ pump, and the excitation of just some of the more basic molecules appears to be sufficient to assist in rearranging the other charge architectures back to their evolution dictated states.

The foregoing effect appears to have some confirmation in scientific literature. For example, Horwitz, L R, Burke, T J, Carnegie, D, 1999. Augmentation of Wound Healing Using Monochromatic Infrared Energy; Exploration of a New Technology for Wound Management. *Advances in Wound Care* 12:35–40 describes the use of 890 nanometer monochromatic light effectively treating recalcitrant dermal lesions and ulcers that sometimes resisted conventional care for more than 39 years. Similarly, living tissue molecular array response to weak electric and magnetic fields has long been recognized. See, e.g., Adey, W R, Bawin, S M Brain Interactions with Weak Electric and Magnetic Fields. *Neurosciences Research Program Bulletin* 15(1):1–129. These and other publications clearly establish an interactive relationship between living tissue and weak electromagnetic fields. Accordingly, a mechanism for conveniently producing such fields that induce response in living tissue including electron state changes is extensively desired and it one such mechanism that is disclosed herein.

SUMMARY OF THE INVENTION

Accordingly, it is the general purpose and object of the present invention to provide a pulsed charge field useful to raise the excitation states of molecular bonding in biological molecules.

Other objects of the invention are to provide a pulsed charge field including frequency spectra in each pulse within the frequency domain of a wet circuit.

Yet further objects of the invention are to provide a pulsed charge circuit completed through the charge architecture of living matter.

Further objects of the invention are to provide a conveniently implemented electrical charge field in circuit with the wet circuit charge architecture of living matter.

Briefly, these and other object are accomplished within the present invention by providing a direct current powered oscillator circuit transformer coupled to a plurality of voltage doubler stages connected to the positive charge terminal that is shaped in the form of a flat plate. The plate, in turn, is enclosed on the exterior surface of a generally flat gas filled chamber that can be pressed to the selected limb or body area of a person with the local charge differential across the chamber then providing localized electrical potentials which effect an energy state change in the gas along with the associated radiation. By selecting a molecular structure of the gas similar to the molecular structures in the adjacent tissue a part of the emitted radiation is then absorbed in the adjacent molecular arrays of the body, raising the excitation levels in the tissue which propagate until a local equilibrium is reached. This equilibrium includes the ambient setting through which the ground return part of the circuit is completed, with the lack of observable radiation then providing an indication that the circuit impedance may be too high, i.e., that the contact skin area may be too dry. In this manner the polar molecules that are associated with all living tissue are included in the circuit lattice responding both to the electrical potential and to the gas emitted radiation.

Those skilled in the art will appreciate that virtually all organic molecules are associated with a distributed electrical charge. Very frequently it is this charge distribution that determines the lobes and foldings of the larger molecules like proteins or peptides and it is the occasional distortions in this charge determined geometry that is often the suspected causative agent associated with disease. Simply, the lobe architecture of a large molecule may be altered by external effects which then alters the molecular interactions with, e.g., receptors, until rearranged to equilibrium state. Of course, the disease consequence associated with distortions in our largest molecules, the chromosomes, are well appreciated at this time and fundamental reasoning dictates that the adjacent smaller molecules will invariably have some effect across the whole range of molecular sizes. It is this effect that is conveniently allowed to resolve itself by the inventive structure disclosed herein.

DESCRIPTION OF THE PREFERRED EMBODIMENT

Figure 1:
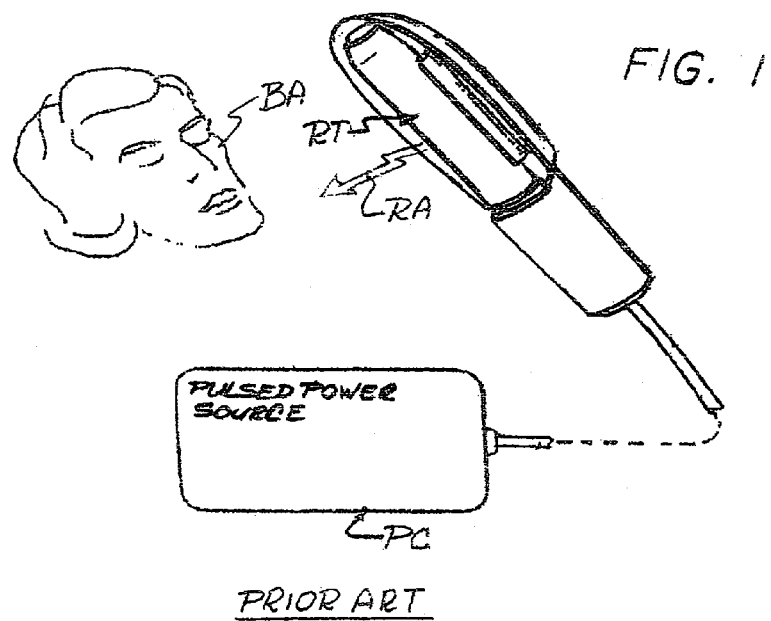
FIG. 1 is a perspective illustration of a prior art gas discharge device useful in emitting light in biologically significant spectra.
Figure 4:
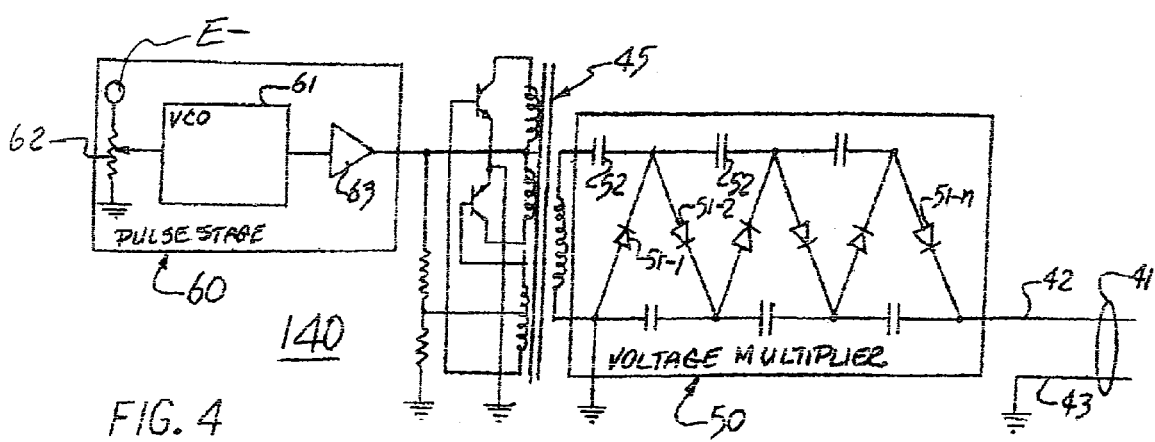
FIG. 4 is a circuit diagram of a pulsed charge circuit useful with the present invention.
Figure 2:
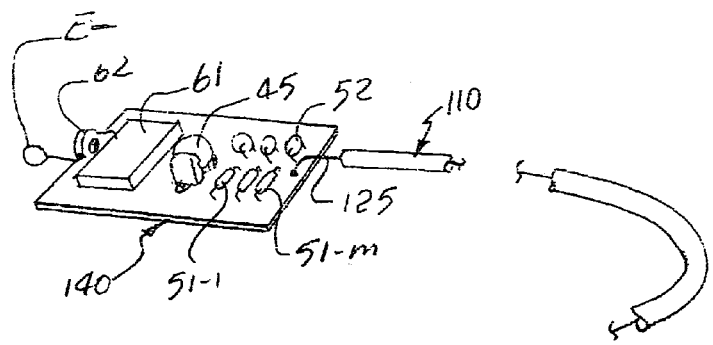
FIG. 2 is a perspective illustration, in partial sections, of the inventive system illustrating the positioning thereof adjacent a selected portion of a user's anatomy.
Figure 2:
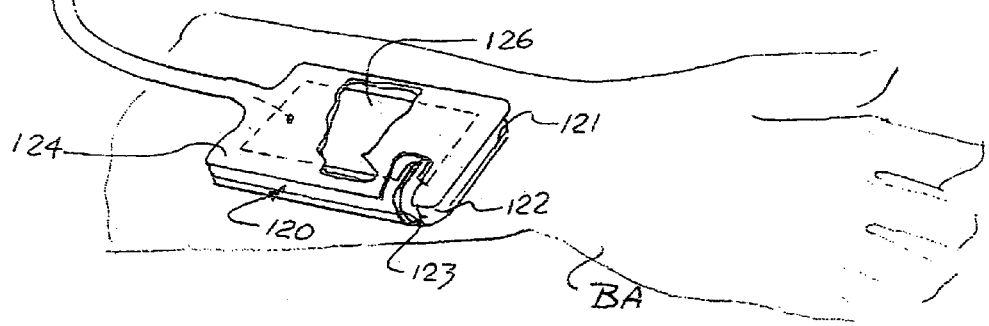

By reference to FIG. 1 my prior U.S. Pat. No. 6,328,760 teaches a pulsed plasma radiation tube RT excited by a pulse circuit PC to ionization potential of the gases contained therein selected to emit radiation RA in biologically significant spectra onto the treated body area BA of a user. To achieve this radiation the gas within the plasma tube RT included molecules like water vapor or H2O, carbon dioxide C2O, molecular nitrogenN2 and perhaps carbonic acid H2CO3 all driven to ionization by the pulse circuit PC. The resulting radiated spectra were then useful in exciting illuminated tissue containing corresponding molecules, or loosely bound components of larger molecules like peptides or proteins, and the higher energy states of these excited molecules would induce, in the manner of a cascade, further state changes propagated through the wet circuit of a cell. In this propagation process any molecular distortions or electrical charge misalignments would be freed up to return to their preferred state. These molecular rearrangement by this ionized gas spectral illumination process have resulted in substantial molecular responses, both useful in promoting healing and in the maintenance of proper homeostasis.

While suitable for the purposes intended and widely useful in the care of various diseases I have since found that the higher potentials of full ionization are not necessary and, in stead, only a sufficient charge difference to obtain an electron state response need be applied. Although not fully understood, it appears that the lattice of polar molecules that are included in all living tissue provides its own charge distributions at the body surface and this distribution may be used to advantage in producing sufficient electric potential to effect an electron state change. Of course, this is associated with a release of radiation which then raises the state of other electrons and this state change then cascades down into the treated tissue through its molecular lattice until all the available state changes can be effected, and so on. In this manner large body areas can be influenced with relatively low electric potentials.

This lower level of charge differential can be conveniently effected by modifying the pulse circuit of my earlier U.S. Pat. No. 6,328,760 and the teachings thereof are incorporated herein. By reference to FIGS. 2 through 5 and by further reference to the teachings of my prior '760 patent, like numbered parts functioning in the like manner to that previously described, the inventive system generally designated by the numeral 110 includes a generally rectangular gas impervious chamber 120 defined by a flat transparent front panel 121 peripherally bonded to the edges of a mating concave rear panel 122 to form a closed cavity 123 therebetween. A conductor 125 is then extended along the exterior of the rear panel 122 deploying a flat sheet electrode 126 over chamber 120 under a sealing membrane 124 adhered to the edges of rear panel 122.

Similar to the teachings of my prior '760 patent chamber 120 may be filled with a gaseous mixture of common molecules like water vapor, carbon dioxide, carbonic acid and the like, each readily brought to a higher excitation state by electrical charge of electrode 126. To develop this charge potential the other end of conductor 125, in turn, connects to a pulsed power source generally designated 140 comprising a pulse stage 60 of similar construction to that shown by the same numeral in my prior '760 patent, gated by a voltage controlled oscillator 61 set in its oscillation frequency by a potentiometer 62 in a voltage divider circuit between the positive signal E+ and ground. The output of oscillator 61 drives to saturation at both limits of an operational amplifier 63 which is then amplified by a power amplifier 65 that is tied to the primary of a transformer 45 the secondary thereof driving a voltage multiplier 150 comprising a lattice of diodes 51-1 through 51-m interconnected by capacitors 52 with the last doubler stage at diode 51-m then connecting to the conductor 125.

In accordance with the present invention the pulse potential EF of conductor 125 is well below the ionization level of the gases in cavity 123 but is sufficient to exceed the bonding potential of the typical outer electrons of organic molecules, e.g., voltages less than 50 volts. Thus only singular electromagnetic packets associated with electron state change are emitted, particularly those containing the spectra of the common molecular states.

It will be appreciated by those skilled in the art that the foregoing pulse circuit is configured substantially like the pulse circuit in the '760 patent. By reducing the number of multiplication stages, however, the effective potential is substantially below that resulting in ionizing disassociation and the effect is primarily one of electric potential or charge. By particular reference to FIG. 3 this charge effect couples with the polar molecules like water WA-1 through WA-r, other polar organic molecules like peptides PE-1 through PE-s, proteins PR-1 through PR-t and so on. In the presence of an electric charge field these will arrange in lattices or arrays AR where the polar difference across this molecular array in the tissue and the molecular lattice of the gas within cavity 123 is less than the potential EF at the electrode 126. The excess electrode potential is then useful to effect an electron state change along with the associated shedding of light that may then excite corresponding molecules WA-1 through WA-r in the tissue array AR which concurrently modifies the remaining array balances and their resulting lattice architecture. In this manner small energy packets are useful in reorganizing tissue structure on a macroscopic level.

Figure 6:
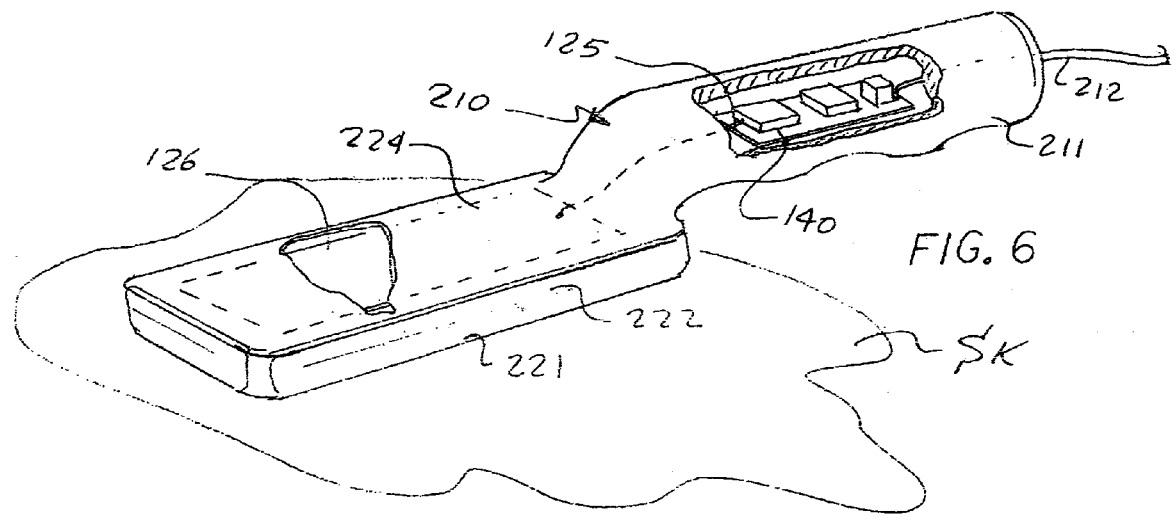
FIG. 6 is a perspective illustration, in partial section of one physical configuration of the inventive pulse charge system conformed as a manual applicator of a geometry that provides the dominant discharge path across the charged cavity.
Figure 3:
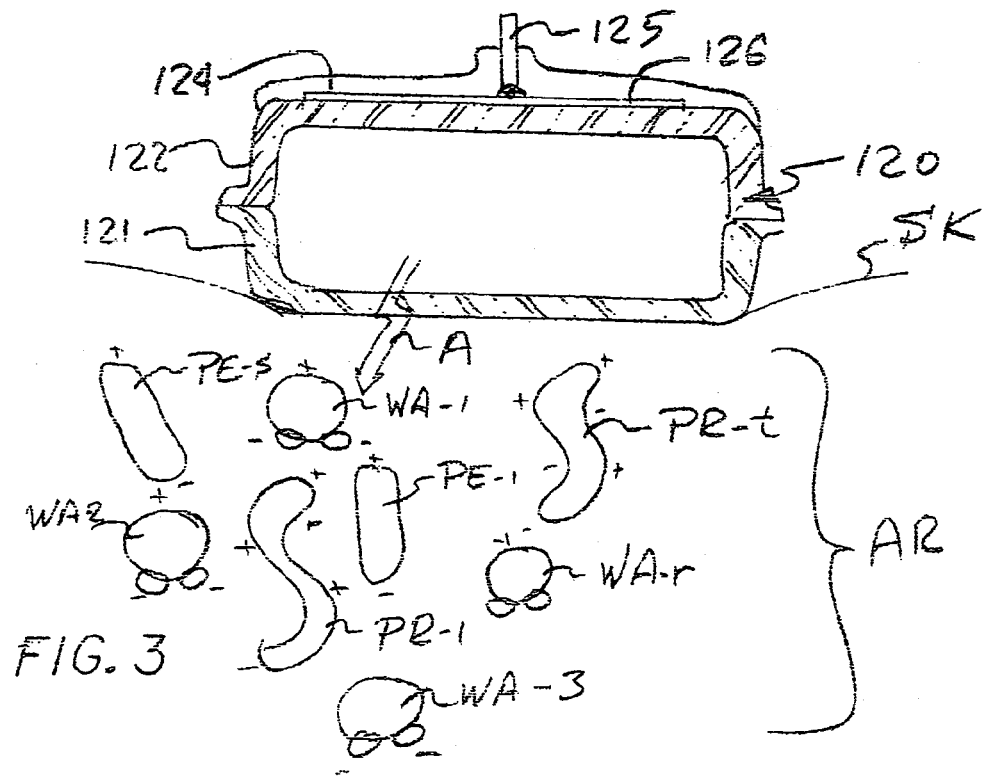
FIG. 3 is an exemplary electro-potential lattice approximating the polar nature of human tissue that is exposed both to a charged field and to light stimulation.
Figure 5:
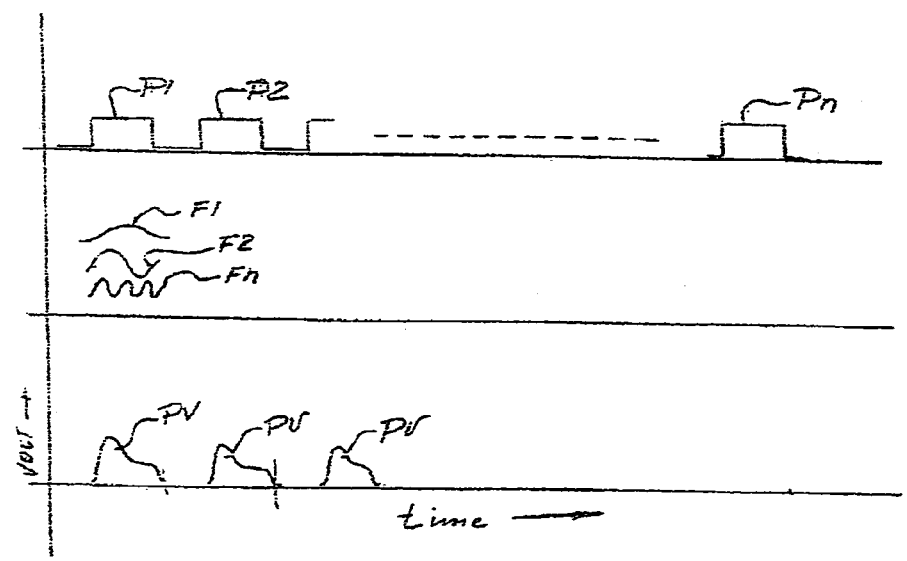
FIG. 5 is a diagrammatic illustration of the pulse shapes provided by the circuit shown in FIG. 4.

Those skilled in the art will appreciate that the foregoing inventive system includes inherent discharge preferences that seek out the shortest discharge paths. To confine these discharge effects to a path across chamber 120, and preferably not across the conductor 125 to ground, an applicator structure is illustrated in FIG. 6 under the generally numbered designation 210 in which like numbered parts function in like manner to those previously described. More precisely, applicator 210 is characterized by a generally cylindrical handle 211 of a substantial radial and longitudinal dimension and a dielectric material selected to insulate the pulsed power source 140 including all the operative components thereof. An electrical lead 212 then extends into handle 211 to provide the power signal E+ to circuit 140 which then generates the sequence of pulses on the output conductor 125 and the rectangular sheet electrode 126. Chamber 120 is formed on the interior of an offset rectangular piece 221 extending in cantilever from handle 211 with the electrode 126 mounted on the rear surface 222 thereof and thereafter sealed by an exterior membrane 224 in this deployment. The front surface 223 of piece 221 can then be manipulated into any desired contact alignment with the skin SK of the user. By selecting the material dielectric coefficients and geometric spacing dimensions this structure insures that the minimal discharge path is across chamber 120, thus insuring that the user's hand UH does not by-pass the desired effect. In this manner the primary result is the one previously described, a result that assists in realigning the various molecular lobe structures of the biological molecules affected.

Of course, other shapes may be devised with particular attention to the body shape that is intended for exposure, such as cavities convolved into toroidal shapes to surround a digit or limb or similar adaptations. In each instance, however, the geometric constraint that needs to be met is one that assures that the minimal discharge path is across the cavity.

Obviously, many modifications and variations can be effected without departing from the spirit of the invention instantly disclosed. It is therefore intended that the scope of the invention be determined solely by the claims appended hereto.

It is claimed:

1. A pulsed charge applicator useful in inducing an increase in the electrical charge state of a biological molecule in human tissue, comprising:

a generally rectangular hollow chamber defined by a transparent front wall and an opposed rear wall enclosing a volume of gas including water vapor and carbon dioxide confined therebetween, said chamber being conformed for intimate contact with the tissue of a person at the front surface thereof;

a planar electrode affixed to the exterior of said chamber in contiguous alignment adjacent said rear wall, said electrode including a conductor connected thereto;

an insulating handle attached to said chamber and conformed to enclose said conductor therein, whereby the preferred path of electrical discharge between said conductor, said electrode and said tissue is across said chamber; and means for producing an electrical pulsed charge connected to a free end of said conductor for producing a sequence of electrical charge pulses of an electrical potential relative the ambient charge level sufficient to excite one or more of the molecules comprising said volume of gas to a higher level of excitation, each occurrence of excitation change producing a discrete electromagnetic pulse, said means for producing an electrical pulsed charge completing the other part of its circuit across ambient space.

* * * * *